United States Patent
Voskrebenzev et al.

(10) Patent No.: US 10,010,293 B2
(45) Date of Patent: Jul. 3, 2018

(54) METHOD OF QUANTITATIVE MAGNETIC RESONANCE LUNG IMAGING

(71) Applicant: Medizinische Hochschule Hannover, Hannover (DE)

(72) Inventors: Andreas Voskrebenzev, Hannover (DE); Marcel Gutberlet, Hannover (DE); Jens Vogel-Claussen, Hannover (DE)

(73) Assignee: MEDIZINISCHE HOCHSCHULE HANNOVER, Hannover (DE)

( * ) Notice: Subject to any disclaimer, the term of this patent is extended or adjusted under 35 U.S.C. 154(b) by 126 days.

(21) Appl. No.: 15/178,894

(22) Filed: Jun. 10, 2016

(65) Prior Publication Data

US 2016/0367200 A1 Dec. 22, 2016

(30) Foreign Application Priority Data

Jun. 16, 2015 (EP) .................... 15001782

(51) Int. Cl.
*G06K 9/00* (2006.01)
*A61B 5/00* (2006.01)
(Continued)

(52) U.S. Cl.
CPC ............ *A61B 5/7282* (2013.01); *A61B 5/004* (2013.01); *A61B 5/055* (2013.01); *A61B 5/08* (2013.01);
(Continued)

(58) Field of Classification Search
CPC ......... A61B 5/0816; A61B 5/055; A61B 5/08; A61B 5/087; A61B 5/113; A61B 5/091;
(Continued)

(56) References Cited

U.S. PATENT DOCUMENTS

| 8,660,634 B2 | 2/2014 | Patz et al. | |
| 2003/0016850 A1* | 1/2003 | Kaufman | G06F 19/321 382/128 |

(Continued)

OTHER PUBLICATIONS

Bauman et al., "Matrix Pencil Decomposition of Time-Resolved Proton MRI for Robust and Improved Assessment of Pulmonary Ventilation and Perfusion", Magnetic Resonance in Medicine 00:00-00 (2016).

(Continued)

*Primary Examiner* — Vu Le
*Assistant Examiner* — Guillermo Rivera-Martinez
(74) *Attorney, Agent, or Firm* — Caesar Rivise, PC

(57) ABSTRACT

A method of processing magnetic resonance (MR) lung images creates a quantitative ventilation map of the lung, which is calculated from ventilation images. A step of determining ventilation frequency includes a frequency analysis of a time series of a quantitative lung dimension parameter which is characteristic for the dimension of the lung at the time of collecting the corresponding MR lung image. Creation of the quantitative ventilation map includes selecting a first group of ventilation images, which consists of expiration ventilation images collected at regular expiration phases of multiple ventilation periods, and a second group of ventilation images, which consists of inspiration ventilation images collected at regular inspiration phases of the multiple ventilation periods, and calculating the quantitative ventilation map from the first and second groups of ventilation images, wherein the quantitative ventilation map is adjusted with reference to the tidal volume of the lung.

9 Claims, 6 Drawing Sheets

(51) Int. Cl.
*A61B 5/08* (2006.01)
*A61B 5/055* (2006.01)
*G06T 5/50* (2006.01)
*G06T 7/00* (2017.01)

(52) U.S. Cl.
CPC .............. *G06T 5/50* (2013.01); *G06T 7/0016* (2013.01); *A61B 2576/02* (2013.01); *G06T 2207/10016* (2013.01); *G06T 2207/10076* (2013.01); *G06T 2207/10088* (2013.01); *G06T 2207/20056* (2013.01); *G06T 2207/20216* (2013.01); *G06T 2207/30061* (2013.01)

(58) Field of Classification Search
CPC ................ A61B 5/7257; A61B 5/0813; G06T 2207/10016; G06T 2207/10088; G06T 2207/30061; G06T 2207/10076; G06T 2207/20056; G06T 2207/30004
See application file for complete search history.

(56) References Cited

U.S. PATENT DOCUMENTS

| | | | | |
|---|---|---|---|---|
| 2012/0215504 | A1* | 8/2012 | Parker | A61B 5/083 703/2 |
| 2012/0319685 | A1* | 12/2012 | Burger | G01R 33/5676 324/309 |
| 2013/0281830 | A1* | 10/2013 | Patz | A61B 5/0205 600/419 |
| 2013/0303899 | A1* | 11/2013 | Mistry | A61B 6/5205 600/425 |
| 2013/0338489 | A1* | 12/2013 | Prisk | A61B 5/055 600/420 |
| 2014/0037169 | A1* | 2/2014 | Fenchel | A61B 5/0035 382/131 |
| 2015/0031979 | A1* | 1/2015 | Rappaport | A61B 5/05 600/407 |
| 2016/0038727 | A1* | 2/2016 | Emami | A61B 5/055 600/420 |
| 2016/0213341 | A1* | 7/2016 | Salcudean | A61B 6/50 |
| 2017/0172527 | A1* | 6/2017 | Uber, III | A61B 6/481 |

OTHER PUBLICATIONS

Avants et al., "A Reproducible Evaluation of ANTs Similarity Metric Performance in Brain Image Registration" in "Neuroimage" vol. 54, No. 3, pp. 2033-2044 (2011).
Bauman et al., "Non-Contrast-Enhanced Perfusion and Ventilation Assessment of the Human Lung by Means of Fourier Decomposition in Proton MRI" in "Magnetic Resonance in Medicine" vol. 62, pp. 656-664 (2009).
Bauman et al., "Pulmonary Functional Imaging: Qualitative Comparison of Fourier Decomposition MR Imaging with SPECT/CT in Porcine Lung", Radiology, vol. 260, No. 2, pp. 551-559, XP055235865 (2011).
Chefd'Hotel et al., "Flows of Diffeomorphisms for Multimodal Image Registration", Proceedings of the IEEE International Symposium on Biomedical Imaging, Washington, USA (2002).
Deimling et al., "Time Resolved Lung Ventilation Imaging by Fourier Decomposition" in "Proc. Intl. Soc. Mag. Reson. Med." vol. 16, pp. 2639 (2008).
Kjorstad et al., "Quantitative lung ventilation using Fourier decomposition MRI; comparison and initial study" in "Magn. Reson. Mater. Phy." pp. 1-10, DOI 10.1007/s10334-014-0432-9 (2014).
Schonfeld et al., "Performance of Perfusion-Weighted Fourier Decomposition MRI for Detection of Chronic Pulmonary Emboli" in "Journal of Magnetic Resonance Imaging", pp. 1-8, electronic publication on Sep. 17, 2014.
Voskrebenzev et al., "Detection of Chronic Allograft Dysfunction using Ventilation-Weighted Fourier Decomposition Lung MRI" in "ISMRM Proceedings", Toronto (2015).
Voskrebenzev et al., "Introduction of global specific ventilation as a reference for specific ventilation derived by Fourier Decomposition MRI" in "ISMRM Proceedings", Milan (2014).
Zapke et al., "Magnetic resonance lung function—a breakthrough for lung imaging and functional assessment? A phantom study and clinical trial" in "Respiratory Research" vol. 7:106, pp. 1-9 (2006).

* cited by examiner

METHOD OF QUANTITATIVE MAGNETIC RESONANCE LUNG IMAGING

This application claims priority under 35 U.S.C. § 119 to European application EP 15001782.0 which is incorporated by reference in its entirety.

TECHNICAL FIELD OF INVENTION

The invention relates to a method of image processing of magnetic resonance (MR) images of a lung (MR lung images) of a subject under investigation for creating a quantitative ventilation map of the lung. In particular, the invention relates to magnetic resonance tomography (MRT) based lung imaging using Fourier decomposition. MR lung images are processed which provide a map of local lung ventilation, without using ionising radiation and without using contrast agents. The invention relates to multiple sub-processes of image processing of the MR lung images, which result in an improved image quality, stability of image calculation and quantification of local distribution of ventilation in the lung. Both, the sub-processes alone and combinations thereof provide subjects of the invention. Applications of the invention are available in medical MR imaging, in particular in quantitative MR lung imaging.

BACKGROUND ART

For illustrating the background of the invention, particular reference is made to the following publications:

[1] C. Chefd'hotel et al. "Flows of Diffeomorphisms for Multimodal Image Matching", Proceedings of the IEEE International Symposium on Biomedical Imaging, Washington, USA (2002);
[2] M. Zapke et al. in "Respiratory Research" vol. 7, 2006, p. 106;
[3] M. Deimling et al. in "Proc. Inti. Soc. Mag. Reson. Med." vol. 16, 2008, p. 2639;
[4] G. Bauman et al. in "Magnetic Resonance in Medicine" vol. 62, 2009, p. 656;
[5] B. B. Avants et al. "Neuroimage" vol. 54, 2011, p. 2033;
[6] A. Kjørstad et al. in "Magn. Reson. Mater. Phy." 2014, p. 1-10 (DOI 10.1007/s10334-014-0432-9);
[7] C. Schönfeld et al. in "Journal of Magnetic Resonance Imaging", electronic publication on Sep. 17, 2014;
[8] A. Voskrebenzev et al. "Introduction of global specific ventilation as a reference for specific ventilation derived by Fourier Decomposition in "ISMRM Proceedings", Milan, 2014;
[9] A. Voskrebenzev et al. "Detection of Chronic Allograft Dysfunction using Ventilation-Weighted Fourier Decomposition Lung MRI" in "ISMRM Proceedings" Toronto, 2015; and
[10] U.S. Pat. No. 8,660,634 B2.

Magnetic resonance tomography (MRT) based lung imaging using Fourier decomposition is described e. g. in [3, 4, 10]. A quantitative ventilation map of the lung can be created by processing MR lung images along the following procedure. A series of two-dimensional (2D) MR lung images is collected with an MRI scanner, e. g. with a temporal resolution of 0.3 s per image for each slice position for a period of 1 min of free ventilation.

Firstly, the MR lung images are subjected to a registration into one image representing a medium ventilation position, using a non-rigid transformation [1, 5] with transformation fields. The registration results in a deformation of the lung images so that all images correspond to the same ventilation position (or: ventilation status). Accordingly, a characteristic temporal signal intensity can be assigned to each lung image voxel.

The registration process as conventionally used in the Fourier decomposition context has the following disadvantages. Images of the expiration ventilation position and the inspiration ventilation position are directly registered into the image representing the medium ventilation position. This requires a strong deformation of lung images resulting in a risk of misregistrations. Furthermore, due to the required temporal resolution, the signal to noise ratio (SNR) of the single images is relatively low. Local lung structures which are important for estimating the transformation fields are superimposed by noise, thus further impeding the registration.

Subsequently, a frequency determination and a separation of ventilation and perfusion contributions in the images is conducted. As the MRI signal is proportional to the proton density, the signal intensity oscillates with the ventilation frequency anti-proportional to the volume change of the lung during the ventilation. Simultaneously, the signal intensity is modulated by blood perfusion with a heart perfusion frequency, which is higher than the ventilation frequency. The ventilation and perfusion frequencies can be determined and separated by a Fourier decomposition of an averaged temporal signal intensity in frequency space [4, 9].

As a limitation of the conventional frequency determination, the averaged temporal signal intensity reliably can be used with healthy subjects only. However, with subjects having a lung disease, abnormal ventilation may occur. This may impede or even exclude an appropriate frequency determination. Furthermore, the Fourier decomposition requires a periodic ventilation and perfusion. With an irregular ventilation, the spectrum of ventilation is broadened in frequency space. Accordingly, the integration limits for calculating the amplitude of ventilation have to be extended, resulting in an increased noise contribution.

Finally, a quantification is obtained by voxel-based integration of image signals at the ventilation and perfusion peaks, resulting in a ventilation or perfusion weighted map of the lung as described in [3] or [4]. Ventilation can be quantified using the parameter fractional ventilation (FV), which is calculated by a ratio of a lung tidal volume (difference of inspiration and expiration volumes) and the inspiration volume.

Conventionally, these volumes are measured e. g. by spirometry. Due to the relationship of signal intensity and volume, it could be considered that this ratio correspondingly can be calculated from the MR lung signal intensities. The integrated ventilation peak would provide the signal change caused by the tidal volume [2]. For calculating the FV, this integration value could be scaled with the expiration signal [6]. However, this approach using MR lung signal intensities does not allow an appropriate quantification process as the fractional ventilation depends on the ventilation deepness, which can vary within the series of MR lung images collected [8]. As the varying ventilation deepness cannot be compensated with the conventional techniques, the calculation of the fractional ventilation based on conventionally processed images cannot yield assessable and reproducible quantitative results.

In summary, the conventional methods mainly suffer from limitations in SNR of registered, filtered and quantified images, so that the conventional quantitative ventilation maps have a limited information contents.

OBJECTIVE OF THE INVENTION

The objective of the invention is to provide an improved method of image processing of MR lung images, which avoids disadvantages of conventional techniques. In particular, the objective of the invention is to provide the method of image processing of MR lung images with increased sensitivity and reproducibility, improved SNR and/or reduced loss of information contributions included in the MR lung images.

SUMMARY OF THE INVENTION

This objective is solved with a method of image processing of MR lung images comprising the features of claim 1. Preferred embodiments and applications of the invention are defined in the dependent claims.

According to a first general aspect of the invention, the above objective is solved by a method of processing MR lung images of a subject under investigation, comprising the steps of providing a series of the MR lung images collected over a time interval covering multiple ventilation periods, registering the MR lung images for creating a series of registered MR lung images, determining a ventilation frequency from the registered MR lung images, creating a series of ventilation images by applying a ventilation frequency based low-pass frequency filter on the registered MR lung images, wherein the ventilation images preferably are independent of (not influenced by) the perfusion of the subject under investigation, and creating a quantitative ventilation map of the lung, which is calculated from the ventilation images.

According to the invention, the step of determining the ventilation frequency includes a frequency analysis of a time series of a quantitative lung dimension parameter (area parameter), the value of which being characteristic for the dimension of the lung (size of the lung) at the time of collecting the corresponding MR lung image. Contrary to the conventional Fourier decomposition of an averaged temporal signal intensity and frequency detection in frequency space, the invention is based on a construction and analysis of the time series of the quantitative lung dimension parameter, i. e. a provision of an oscillating lung area quantity in time space. Advantageously, analysing the time series of the quantitative lung dimension parameter allows determining the ventilation frequency with increased reliability and stability, compared with conventional analysing of signal intensity oscillations.

Furthermore, according to the invention, the step of creating the quantitative ventilation map includes selecting a first group of ventilation images, which consists of expiration ventilation images collected at regular expiration phases of the multiple ventilation periods, selecting a second group of ventilation images, which consists of inspiration ventilation images collected at regular inspiration phases of the multiple ventilation periods, and calculating the quantitative ventilation map from the first and second groups of ventilation images.

The inventors have found, that multiple ventilation periods of healthy or sick subjects include expiration and inspiration phases (or: expiration and inspiration events), which can be assigned to a regular ventilation (or: periodic, continuous ventilation). The regular expiration and inspiration phases can be identified in particular on the basis of the improved ventilation frequency determination of the invention. Expiration ventilation images collected at the regular expiration phases and inspiration ventilation images collected at the regular inspiration phases are selected for creating the quantitative ventilation map, while ventilation images of irregular ventilation phases are discarded. Furthermore, the quantitative ventilation map is adjusted with reference to the tidal volume of the lung. Advantageously, this avoids any dependency of the quantification process on the ventilation deepness.

Advantageously, the SNR of the ventilation images is improved due to the improved determination of the ventilation frequency and the selection of images representing the regular ventilation. The quantitative ventilation map obtained with the invention includes more reliable information compared with conventional techniques. In particular, the quantitative ventilation map is an image wherein the intensity (brightness of the image pixels) is a direct measure for the local ventilation. On the basis of the local ventilation information, the quantitative ventilation map created according to the invention can be evaluated by a physician in a separate step, in particular for characterizing the health status of the subject or finding a diagnosis.

According to a second general aspect of the invention, a method of magnetic resonance imaging of a lung is disclosed, comprising the steps of collecting a series of MR image raw data for obtaining multiple MR lung images, and subjecting the MR lung images to an image processing according to the above first aspect of the invention.

According to preferred embodiments of the invention, the quantitative lung dimension parameter used with the inventive method of processing MR lung images is at least one of a lung area value of the registered MR lung images and an averaged ROI signal value of a region of interest covering a part of the lung and a part of the adjacent thoracic diaphragm of the subject under investigation.

According to the first variant, lung area values are obtained by applying inverse transformation fields from the registered image series to one initial ROI outlining the lung parenchyma. Thus, ROIs for each time point of the registered image series can be obtained and the lung area value time series can be determined using the inverse transformation fields. This information can be used not only for the stable determination of the ventilation frequency, but also for the determination of the inspiration and expiration events and for the scaling of the FV as outlined below.

According to the second variant, using the averaged ROI signal value is based on the following consideration. Due to different proton densities, the lung and the thoracic diaphragm provide substantially different MRI signals. The ROI is arranged such that the portion of the lung within the ROI is changing in dependency on the ventilation position. Accordingly, the averaged MRI signal of the ROI directly follows the ventilation.

According to a particularly preferred embodiment of the invention, the first and second groups of ventilation images are selected by retrospective gating of the time series of the quantitative lung dimension parameter. The retrospective gating comprises an assignment of the values of the measured quantitative lung dimension parameter to predetermined intervals of the quantitative lung dimension parameter (gating) and a determination of regular ventilation events by counting the number of assigned values in each interval. The intervals with maximum numbers of assigned values and the ventilation images associated with the values assigned to those maximum intervals are provided as regular ventilation phases. Advantageously, the retrospective gating (navigator) allows a targeted selection of ventilation images with similar ventilation deepness and a maximization of the SNR. Preferably, the retrospective gating uses the same quantitative lung dimension parameter like the ventilation frequency determination, in particular the lung area value or the averaged ROI signal value. Thus, the processing complexity is reduced. Alternatively, the retrospective gating and the ventilation frequency determination use different quantitative lung dimension parameters.

According to a further preferred embodiment of the invention, the step of calculating the quantitative ventilation map includes calculating a fractional or specific ventilation image obtained from a difference between an averaged expiration image from the first group of ventilation images and an averaged inspiration image from the second group of ventilation images, divided by the averaged inspiration or expiration ventilation image. Particularly preferred, the quantitative ventilation map is calculated by adjusting (or: scaling) the fractional ventilation image with reference to the tidal volume of the lung, using a global fractional ventilation parameter, wherein the global fractional ventilation parameter is calculated from the lung area values of the averaged inspiration and expiration images or from measured ventilation flow values.

According to a further particularly preferred embodiment of the invention, the step of registering the MR lung images comprises assigning the collected MR lung images into groups (or: classes), wherein all collected MR lung images within each one of the groups have the quantitative lung dimension parameter, in particular the averaged ROI signal value, within a common predetermined parameter interval, group-wise registering the collected MR lung images within the groups of collected MR lung images, and step-wise registering the group-wise registered MR lung images or an averaged MR lung image thereof, starting from parameter intervals corresponding to expiration and inspiration ventilation positions towards a parameter interval corresponding to an intermediate ventilation position. Preferably, the intermediate ventilation position is a medium ventilation position between expiration and inspiration.

Advantageously, the problems of the conventional registration are solved by the present group- and step-wise image registration into reference images from neighbouring ventilation phases. Strong deformations of the images and misregistrations are avoided. As a particular advantage, the group- and step-wise image registration avoids artefacts which otherwise would impair the subsequent steps of ventilation frequency determination and quantification. While the conventional registration may result in wrong conclusions or undiscovered pathologic findings, the inventive registration reduces this risk and even accelerates the registration process.

The inventive step-wise registration of dynamic time series of MR images within groups can be applied not only in combination with the inventive method of processing MR lung images but rather generally for registering time series of MR images. Thus, it is emphasized that the proposed registration process provides an independent subject of the invention wherein the registering the MR images comprises providing groups of a time series of subsequent MR images, the MR images within each group having a quantitative dimension parameter within a common predetermined parameter interval, groupwise registering the collected MR images within the groups of collected MR images, and registering the group-wise registered MR images or an averaged MR image thereof, starting from parameter intervals corresponding to extrema image positions towards a parameter interval corresponding to an intermediate image position.

According to a further general aspect of the invention, an MRI device is disclosed, which is configured for creating a sequence of MR images of an object under investigation. The MRI device comprises an MRI scanner including a main magnetic field device, at least one radiofrequency excitation coil, magnetic field gradient coils and at least one radiofrequency receiver coil, and a control device being adapted for controlling the MRI scanner for collecting the series of sets of image data and for processing the sequence of MR images with the method according to the above first aspect of the invention.

Further general subjects of the invention are a computer program residing on a computer-readable medium, with a program code which, when executed on a computer, carries out the method(s) according to the above first and/or second aspect of the invention, and/or an apparatus comprising a computer-readable storage medium containing program instructions which, when executed on a computer, carry out the method(s) according to the above first and/or second aspect of the invention.

It is noted that the concept of the invention correspondingly can be used for calculating a quantitative perfusion image or perfusion map. Perfusion images which are independent of ventilation of the subject under investigation can be created by applying a high-pass filter on the registered MR lung images in frequency space. Selected perfusion images can be found and analysed which represent a regular heartbeat, for imaging systole and diastole in time space.

BRIEF DESCRIPTION OF THE DRAWINGS

Further details and advantages of the invention are described in the following with reference to the attached drawings, which show in.

EMBODIMENTS OF THE INVENTION

Embodiments of the invention are described in the following with reference to the successive sub-processes of image processing of dynamic 2D MR lung images collected e. g. with coronal or sagittal slices of the lung, resulting in a two-dimensional quantitative ventilation map of the lung. For obtaining a three-dimensional quantitative ventilation map, in particular covering the whole lung, the inventive processing is repeated with further time series of 2D MR lung images representing further coronal or sagittal slices of the lung.

Alternatively, three-dimensional (3D) MR lung images can be collected and subjected to the sub-processes as outlined in the following.

According to FIG. 1, the method of the invention comprises the steps of providing the series of MR lung images (S0), registration (S1), frequency determination (S2), separation of ventilation and perfusion (S3), and quantification (S4), which are described in the following with further details.

(S0) Providing the MR Lung Images

Figure 10:
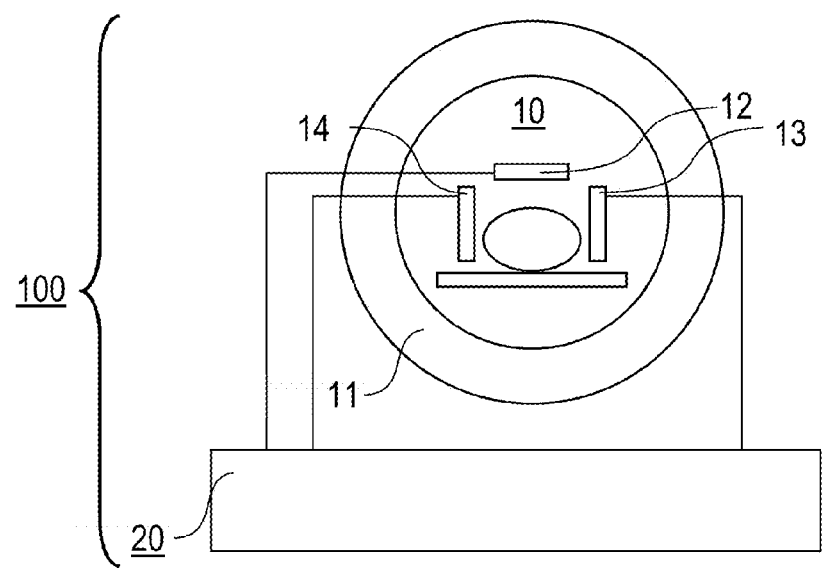
FIG. 10: a schematic illustration of an MRI device according to an embodiment of the invention.

Step S0 of providing the series of MR lung images preferably comprises collecting the MR lung images with an MRI scanner (see e. g. FIG. 10), so that the image data can be directly processed for an output of the quantitative ventilation map of the lung by the MRI scanner. Details of collecting the MR lung images, operating an MRI scanner, the numerical implementation of the mathematical formulation using available software tools and optional further image pre- or post-processing steps are not described as far as they are known from conventional MRI techniques. In particular, usual MRI pulse sequences can be applied for collecting the images, without changes of the commercially available sequences. The number of images, temporal resolution and collecting period can be selected in dependency on the application of the invention. As an example, about 200 images are collected with a temporal resolution of 0.3 s per image and slice position for a collecting period of about 1 min of free ventilation.

Alternatively, the series of MR lung images can be provided separately from collecting the MR lung image data. Previously collected images can be stored and provided, e. g. via a data communication network to a distant processor for implementing the image processing according to the invention.

(S1) Registration

Figure 2:
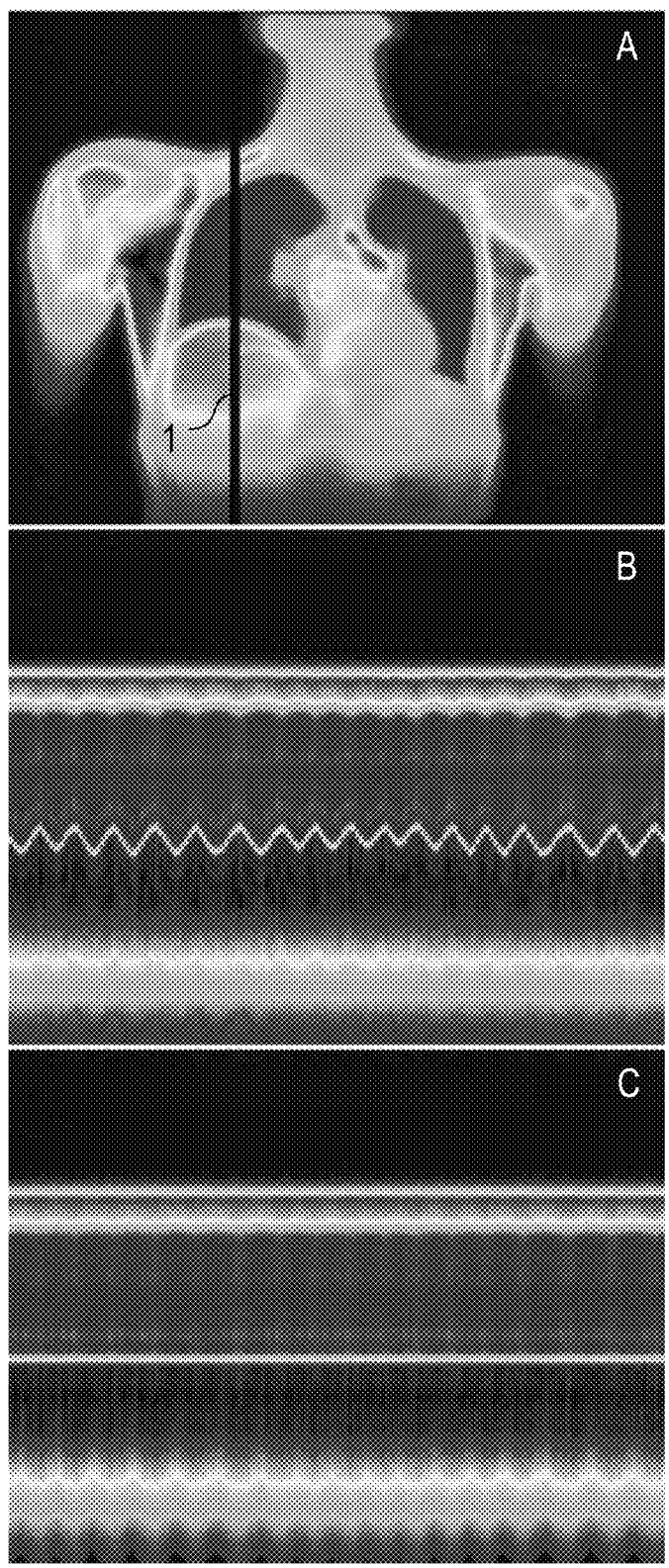
FIGS. 2 and 3: schematic illustrations of an image registration.

The collected lung images are subjected to the registration for deforming the lung images such that they correspond to the same ventilation position. FIG. 2 illustrates the effect of image registration. View A of FIG. 2 shows an MR thorax image wherein the vertical black line 1 represents a cross-section line through the thoracic diaphragm. Before the registration, a periodic diaphragm oscillation is obtained resulting from the ventilation, as shown in view B of FIG. 2. After the registration, the diaphragm oscillation is no longer detectable, as shown in view C of FIG. 2. This deformation can be obtained by a conventional registration, as described e. g. in [2, 4]. However, preferably, the registration is implemented with the following inventive procedure, described with reference to FIGS. 3 and 4.

Figure 3:
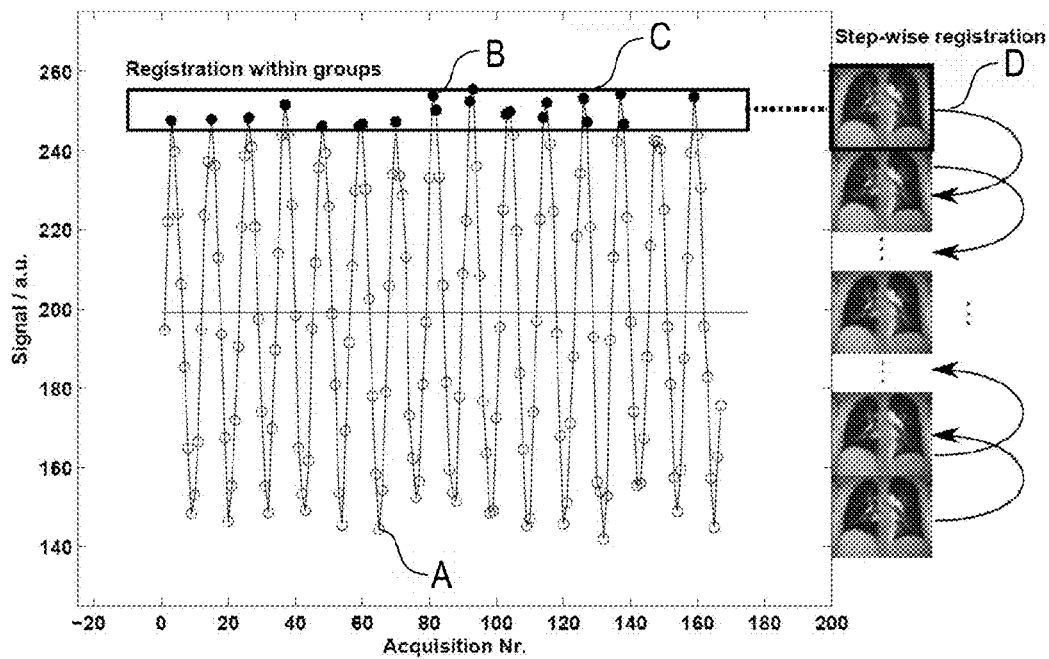
Figure 4:
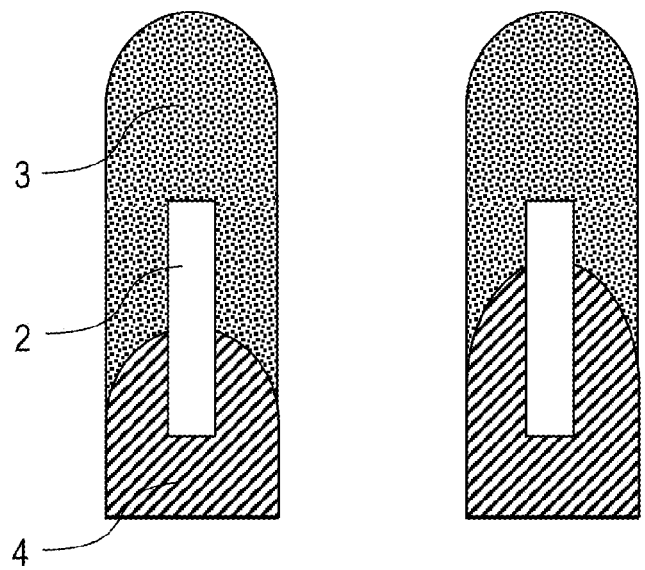
FIGS. 4 and 5: schematic illustrations of measuring quantitative lung dimension parameters.

FIG. 3 shows a ventilation position curve formed by a time dependency of a quantitative parameter representing the current ventilation position for each image acquisition. As an example, the quantitative parameter is an averaged signal of a region of interest (ROI) 2 covering a part of the lung 3 and a part of the adjacent thoracic diaphragm 4 of the subject under investigation, as schematically shown in FIG. 4.

As the lung parenchyma has a low proton density, the image signals of the lung parenchyma are substantially lower compared with the thoracic diaphragm. Due to the movement of the thoracic diaphragm 4, the averaged signal increases during exhalation and decreases during inhalation. Accordingly, the averaged signal of the ROI 2 covering both tissues has a minimum value at inspiration (e. g. A in FIG. 3) and a maximum value at expiration (e. g. B in FIG. 3).

Based on the ventilation position curve of FIG. 3, the registration comprises the following registration steps. Firstly, the ventilation position of each image acquisition is obtained from the averaged ROI signal value of ROI 2.

Subsequently, a plurality of N groups is defined each representing a similar ventilation position. Each group is defined by a specific interval of the averaged ROI signal value of ROI 2, or alternatively by a predetermined number of images with similar ventilation positions. The groups including the ventilation positions of maximum inspiration and expiration are correspondingly indicated as inspiration and expiration groups. Each of the collected MR lung images is assigned to one of the N groups. The value N, e. g. in a range from 5 to 20, is selected in dependency on the particular application conditions such that a number of images is included in each group. In particular, the value N is selected e. g. in consideration of the SNR of the single images (depending on the pulse sequence used for collecting the MR images), the temporal resolution (also depending on the pulse sequence) and the deepness and frequency of ventilation (depending on the subject).

Subsequently, the images within each group are registered into one selected image of the respective group as schematically illustrated in the right part of FIG. 3. The selected image can be found by calculating a similarity parameter for each image relative to the remaining images within the group. The similarity parameter can be calculated with the same metric as used for the registration. The image having the best similarity with the remaining images of the group is used as the selected target image for the registration. The registered images within each group are averaged, so that one averaged group image is assigned to each group. N averaged group images are obtained, one of them representing an intermediate ventilation position.

Finally, each of the averaged group images is registered into the averaged group image of the neighbouring group, starting from the inspiration and expiration groups towards the intermediate ventilation position. Preferably, the intermediate ventilation position is a medium ventilation position between maximum expiration and inspiration. As an example, the averaged group image of group C in FIG. 3 is registered into the averaged group image of the neighbouring group, see arrow D in FIG. 3. In other words, the averaged group images are used for a step-wise registration towards the intermediate ventilation position. As an alternative, the registration can be done into a selected ventilation position other than the medium ventilation position.

Advantageously, this procedure minimizes misregistrations. Combining images into groups allows the averaging of the images, so that the SNR of the images to be registered is increased and the reliability of the registration is improved.

If the images within the groups are sufficiently similar, the registration within the group can be omitted.

As a result of the registration (S1), a series of N transformations fields (and corresponding inverse transformation fields) and N associated registered MR lung images is obtained, which are independent on ventilation movements of the lung.

(S2) Frequency Determination

With step S2 of FIG. 1, the ventilation frequency is determined from a time series of a quantitative lung dimension parameter as outlined in the following with reference to two exemplary embodiments.

According to a first variant, the averaged ROI signal value of the ROI 2 covering a part of the lung 3 and a part of the adjacent thoracic diaphragm 4 of the subject under investigation provides the quantitative lung dimension parameter, as schematically shown in FIG. 4 and described above. The ventilation frequency is directly determined from the ventilation position curve of FIG. 3.

According to a second variant, a time series of lung area values obtained on the basis of the registered MR lung images provides the quantitative lung dimension parameters. Firstly, the left and right lung of the medium ventilation position image obtained after the registration are segmented. Segmentation of the lung parenchyma is done manually or automatically by excluding vessels, in particular large vessels impairing a lung area estimation. The lung area is measured e. g. with the number of pixels covered by the segmented lung.

Figure 5:
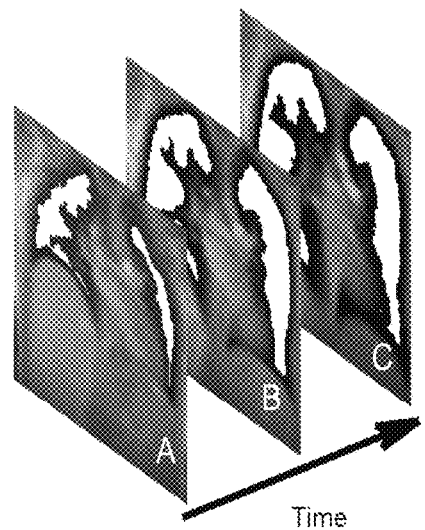

Subsequently, the time series of the lung area is obtained by applying the inverse transformations fields of the registration on the lung ROI for all image acquisitions. FIG. 5 shows an example of lung images for calculating the lung area time series, including an expiration image (A), a medium ventilation position image (B) and an inspiration image (C). A complete lung area time series is obtained by applying the inverse transformations fields on the segmented lung ROI. The ventilation frequency is directly determined from the time series of the lung area values.

Determining the ventilation frequency according to the second variant has particular advantages as the change of the lung area has better stability and reliability compared with the analysis of the averaged ROI signal value of the ROI 2, which can be influenced by irregular ventilation. In particular, the second variant uses morphologic information rather than the anti-proportionality of the MRI signal and lung volume.

(S3) Separation of Ventilation and Perfusion

Figure 1:
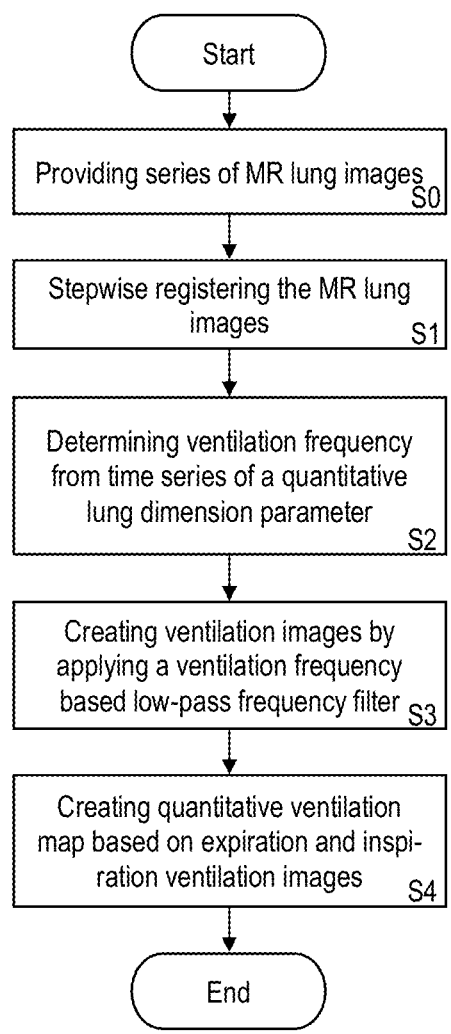
FIG. 1: a flowchart illustrating features of preferred embodiments of the inventive image processing method.

Step S3 of FIG. 1 includes two sub-steps, wherein ventilation images are created by applying a ventilation frequency based low-pass frequency filter in a first sub-step and ventilation images representing regular ventilation are selected from the collected MR lung images in a second sub-step.

The series of ventilation images is created by applying the ventilation frequency based low-pass frequency filter on the registered MR lung images in frequency space. The low-pass frequency filter is provided based on the ventilation frequency determined in step S2. The ventilation images obtained are independent of perfusion of the subject under investigation. The low-pass frequency filter is provided such that frequency contributions at the ventilation frequency are passed, while perfusion contributions, in particular with frequencies near the heart beat frequency, e. g. around 1 Hz are blocked.

Figure 6:
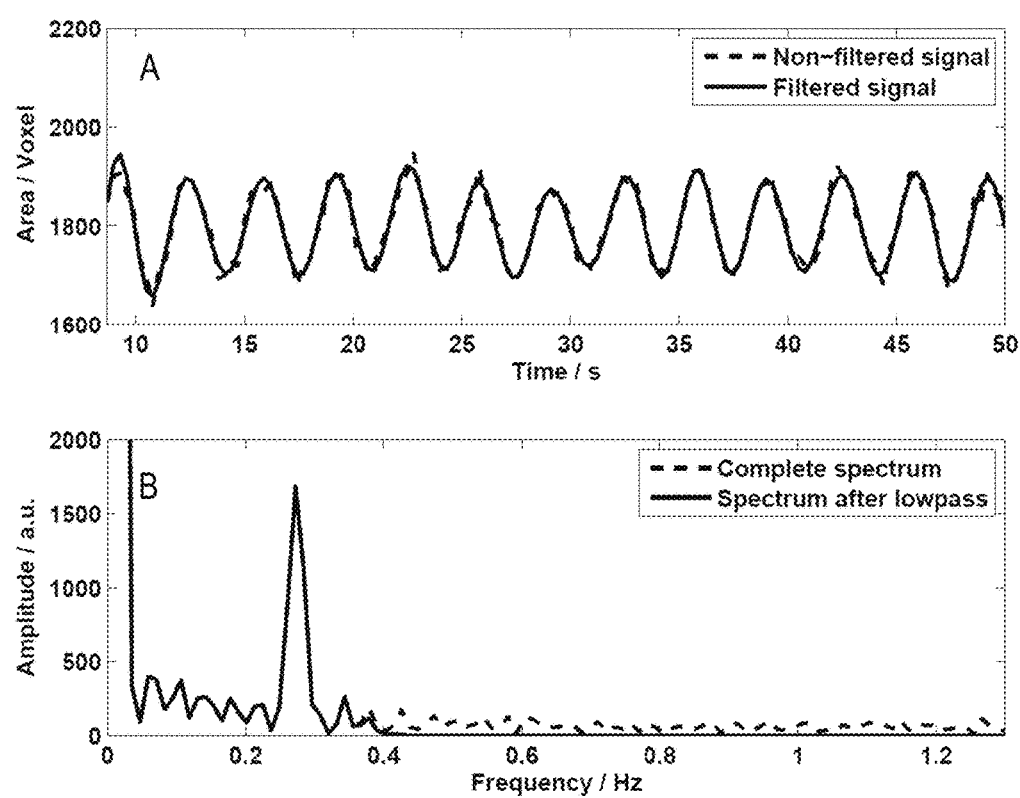
FIG. 6: a schematic illustration of determining a ventilation frequency.

FIG. 6A illustrates the effect of the low-pass filter applied on a time series of the lung area values. The filtered lung area values are smoothed compared with the non-filtered lung area values. FIG. 6B shows a spectrum before and after applying the low pass filter on the area time series. The ventilation frequency can be found with a peak near 0.3 Hz. A perfusion contribution does not occur in FIG. 6B as the lung area time series is used instead of the MR image signal.

FIG. 7A illustrates the effect of the low-pass filter applied on a time series of the lung parenchyma signal (exemplary signal of one lung voxel). The filtered lung parenchyma signal does not contain the perfusion signal variations. FIG. 7B shows a spectrum before and after applying the low pass filter on the image data. The ventilation frequency can be found with a peak near 0.3 Hz. The perfusion frequency can be found with a peak near 1.1 Hz.

Additionally or alternatively, a series of perfusion images can be created by applying a high-pass filter on the registered MR lung images in frequency space. The high-pass frequency filter is provided based on a perfusion frequency determined by an analysis of a time series of a vessel ROI in analogy to step S2.

Figure 8:
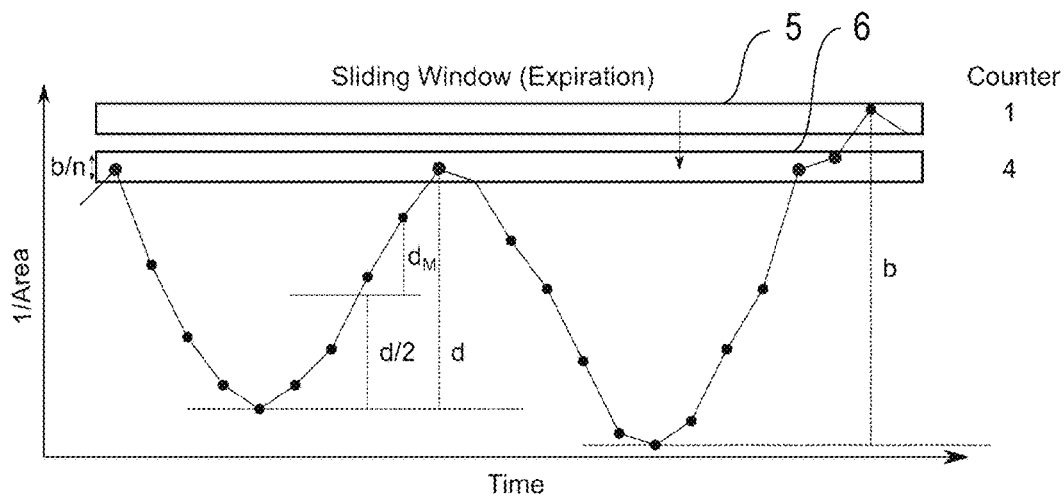
FIG. 8: a schematic illustration of retrospective gating.

Subsequently, the ventilation images are screened for selecting exclusively those ventilation images representing regular expiration and inspiration phases. This is obtained by retrospective gating as illustrated in FIG. 8. The ventilation images of the regular expiration and inspiration phases can be processed with optimized SNR, resulting in an improved quantification result in step S4.

The dynamic change of the (lowpassed) quantitative lung dimension parameter (see FIG. 6), like the lung area or the averaged signal of the ROI 2 (see FIG. 4) is presented in a ventilation position curve. It is noted that the retrospective gating is not restricted to the analysis of the lung area time series, but rather also possible with a time series of another quantitative lung dimension parameter.

FIG. 8 shows an example of implementing the retrospective gating on the basis of a lung area time series as obtained in step S2. As the MR image signal is invers relative to the volume, the lung area time series A(t) is converted into a time series of inverted lung areas A'(t)=1/A(t). Thus, the ventilation position curve includes the inverted lung area values in dependency on time (or number of acquisition). The bandwidth b of inverted lung areas is b=max (A'(t))−min(A'(t)).

A sliding window is defined having a window width, which is determined by the ratio b/n of bandwidth b and a free parameter n. The free parameter n is selected in a range of e. g. 5 to 20, and it is selected in dependency on the particular application conditions as mentioned above with reference to the selection of N in step S1.

The first window 5 (first expiration window, see FIG. 8) extends from max(A'(t)) to [max(A'(t))−b/n]. Each point in A'(t) corresponds to one MR lung image of the dynamic series of MR lung images. All images within a common window are marked as associated expiration images. Subsequently, the expiration window 5 is shifted towards the medium ventilation position. The step width of the sliding window is selected in dependency on the particular application conditions. With each position of the sliding window, the associated expiration images are marked. The window, e. g. window 6 in FIG. 8, having the maximum number of expiration images (see counter) is considered as the expiration window representing a regular ventilation.

The same process, including shifting the sliding window starting from the maximum inspiration towards the medium ventilation position and counting the number of associated inspiration images, is conducted for finding the inspiration window representing the regular ventilation.

Preferably, shifting the sliding window towards the medium ventilation position is restricted by a predetermined first threshold value above or below the inverted lung area corresponding to the medium ventilation position. Advantageously, assignments of expiration images to inspiration windows or vice versa is avoided by applying the threshold value.

Figure 7:
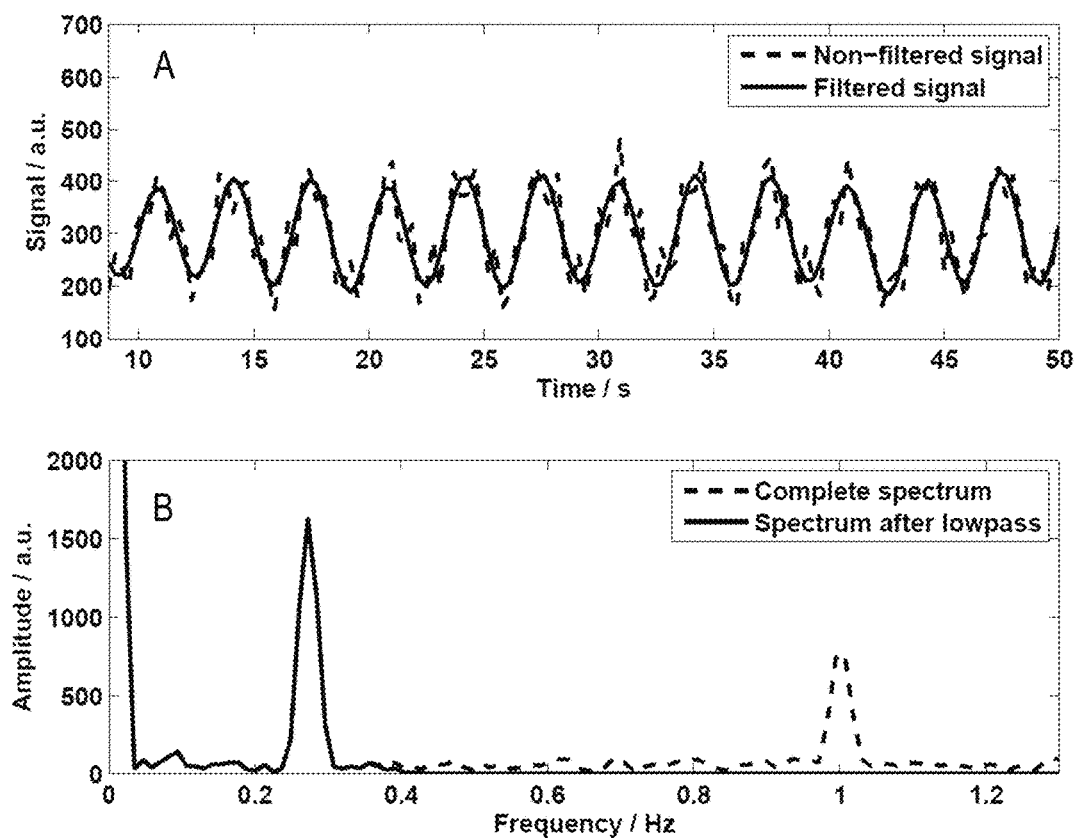
FIG. 7: a schematic illustration of low-pass filtering of a lung parenchyma signal.

As the medium ventilation position can drift during ventilation, a second threshold value h can be introduced as a condition for assigning data points of inverted lung area to the current sliding window. Data points are discarded if the second threshold value h=$d_M$/d (measured in units of A'(t)) goes below a predetermined value. As illustrated in FIG. 7, d is the distance between the adjacent extrema of a considered data point, and $d_M$ is the distance between the considered data point and the local medium ventilation position. As an example, the condition is h≥0.3. Advantageously, the second threshold value h ensures that the expiration and inspiration images of regular expiration and inspiration phases are physiologic real conditions.

As a result of step S3, a first group of selected expiration ventilation images and a second group of inspiration ventilation images are obtained, which represent expiration and inspiration at regular ventilation. Intermediate ventilation positions or extreme ventilation positions having particularly deep or shallow ventilation are discarded. With an example, the selected ventilation images comprise about 10% to 15% of the registered, low-pass filtered MR lung images.

(S4) Quantification

Step S4 includes the calculation of the quantitative ventilation map using the selected expiration and inspiration ventilation images obtained with step S3.

Firstly, all images of the first group of selected expiration ventilation images are averaged, and all images of the second group of inspiration ventilation images are averaged, thus providing one averaged expiration ventilation image and one averaged inspiration ventilation image. The signal intensities of the individual pixels of the averaged expiration and inspiration images are determined by the local ventilation. Accordingly, a fractional ventilation image or FV map is calculated as a quotient of a difference between the averaged expiration and inspiration images and the averaged inspiration or averaged expiration image.

The fractional ventilation image represents a quantitative ventilation map already, which however still depends on the deepness of ventilation. According to a preferred embodiment of the invention, a further adjustment is introduced by calculating a scaled fractional ventilation image or $FV_A$ map, which is normed relative to the lung area. To this end, a global fractional ventilation $FV_A$ value is calculated using the time series of the quantitative lung dimension parameter, in particular the lung area values, of the selected expiration and inspiration ventilation images at regular ventilation. As an example, $FV_A$ is calculated from the difference between the averaged lung area at expiration and the averaged lung area at inspiration divided by the averaged lung area at inspiration or expiration. As an alternative, $FV_A$ can be measured, e. g. by collecting 3D MR lung images, optionally combined with spirometer measurements and analysing lung volume changes.

The scaled fractional ventilation image or $FV_A$ map is calculated by dividing the fractional ventilation image by the global fractional ventilation $FV_A$ value. The scaled fractional ventilation image is a dimensionless quantity which advantageously is independent on ventilation deepness or tidal volume.

Figure 9:
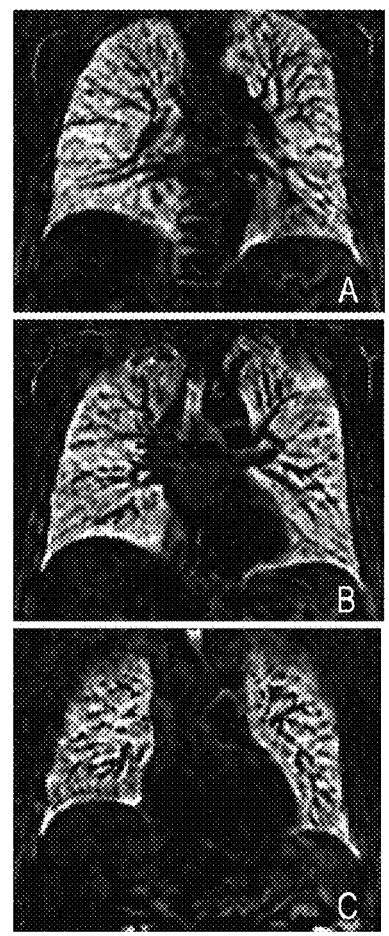
FIG. 9: experimental results obtained with the invention.

FIG. 9 illustrates a scaled fractional ventilation image obtained with the invention in an exemplary manner. Views A, B, and C of FIG. 9 represent three coronal slices of the lung, wherein the vessels can be seen with black images sections and the intensity if ventilation is represented by the brightness of the pixels. As an essential advantage of the invention, the images provide an information on the local ventilation, which was not available with conventional techniques.

Embodiment of MRI Device

FIG. 10 schematically shows an example of an MRT device 100 with an MRI scanner 10 including a main magnetic field device 11, at least one radiofrequency excitation coil 12, at least two magnetic field gradient coils 13 and radiofrequency receiver coils 14. Furthermore, the MRI device 100 includes a control device 20, like a computer circuit, being adapted for controlling the MRI scanner 10 for collecting the series of sets of image raw data and processing the image data with the method according to the invention.

The features of the invention disclosed in the above description, the drawing and the claims can be of significance both individually as well as in combination or subcombination for the realisation of the invention in its various embodiments.

What is claimed is:

1. A method of processing magnetic resonance (MR) lung images of a subject under investigation, comprising the steps of
providing a series of the MR lung images collected during multiple ventilation periods,
registering the MR lung images for creating a series of registered MR lung images,
determining a ventilation frequency from the registered MR lung images,
creating a series of ventilation images by applying a ventilation frequency based low-pass frequency filter on the registered MR lung images, and
creating a quantitative ventilation map of the lung, which is calculated from the ventilation images, wherein
the step of determining the ventilation frequency includes a frequency analysis of a time series of a quantitative lung dimension parameter which is characteristic for the dimension of the lung at the time of collecting the corresponding MR lung image, and
the step of creating the quantitative ventilation map includes
selecting a first group of ventilation images, which consists of expiration ventilation images collected at regular expiration phases of the multiple ventilation periods,
selecting a second group of ventilation images, which consists of inspiration ventilation images collected at regular inspiration phases of the multiple ventilation periods, wherein the first and second groups of ventilation images are selected by retrospective gating of the time series of the quantitative lung dimension parameter, said retrospective gating comprising an assignment of the values of the measured quantitative lung dimension parameter to expiration or inspiration intervals of the quantitative lung dimension parameter and a determination of regular ventilation events by counting the number of assigned values in each expiration or inspiration interval, wherein the ventilation images being associated with the expiration or inspiration intervals with maximum counted numbers of assigned values are respectively provided as the expiration or inspiration ventilation images collected at the regular ventilation phases, and
calculating the quantitative ventilation map from the first and second groups of ventilation images, wherein the quantitative ventilation map is adjusted with reference to the tidal volume of the lung.

2. The method of processing MR lung images according to claim 1, wherein
the quantitative lung dimension parameter is at least one of a lung area value of the registered MR lung images and an averaged ROI signal value of a region of interest covering a part of the lung and a part of the adjacent thoracic diaphragm of the subject under investigation.

3. The method of processing MR lung images according to claim 1, wherein the step of calculating the quantitative ventilation map includes
calculating a fractional ventilation image obtained from a difference between an averaged expiration image from the first group of ventilation images and an averaged inspiration image from the second group of ventilation images, divided by the averaged inspiration or expiration ventilation image.

4. The method of processing MR lung images according to claim 3, wherein the quantitative ventilation map is calculated by adjusting the fractional ventilation image using a global fractional ventilation parameter, wherein the global fractional ventilation parameter is calculated from the lung area values of the averaged inspiration and expiration images or from at least one of measured 3D volume images and measured ventilation flow values.

5. The method of processing MR lung images according to claim 2, wherein the step of registering the MR lung images comprises providing groups of collected MR lung images, wherein the collected MR lung images within each group have the averaged ROI parameter value within a common predetermined parameter interval, group-wise registering the collected MR lung images within the groups of collected MR lung images, and registering the group-wise registered MR lung images or an averaged MR lung image thereof, starting from parameter intervals corresponding to expiration and inspiration ventilation positions towards a parameter interval corresponding to an intermediate ventilation position.

6. The method of processing MR lung images according to claim 5, wherein the intermediate ventilation position is a medium ventilation position between expiration and inspiration.

7. A method of MR imaging the lung of a subject under investigation, comprising the steps of MR image acquisition for collecting MR lung images, and subjecting the MR lung images to a method of processing MR lung images according to claim 1.

8. A computer program residing on a non-transitory computer-readable medium, with a program code which, when executed on a computer, carries out the method according to claim 1.

9. An apparatus comprising a non-transitory computer-readable medium containing program instructions which, when executed on a computer, carry out the method according to claim 1.

* * * * *